United States Patent [19]

Ruck

[11] Patent Number: 4,774,723
[45] Date of Patent: Oct. 4, 1988

[54] WELDING MASK LENS SPRING AND FLASH BARRIER

[75] Inventor: Heinz Ruck, Media, Pa.

[73] Assignee: The Fibre Metal Products Company, Concordville, Pa.

[21] Appl. No.: 20,716

[22] Filed: Mar. 2, 1987

[51] Int. Cl.⁴ .............................................. A61F 9/06
[52] U.S. Cl. ........................................................ 2/8
[58] Field of Search .................... 2/8, 9, 11, 429; 219/147

[56] References Cited

U.S. PATENT DOCUMENTS

| | | | |
|---|---|---|---|
| 1,885,426 | 11/1932 | Flood | 2/8 |
| 2,180,216 | 11/1939 | Snodgrass | 2/8 |
| 3,112,490 | 12/1963 | Malcom, Jr. | 2/8 |
| 3,444,561 | 5/1969 | Boyer | 2/8 |

Primary Examiner—Peter Nerbun
Attorney, Agent, or Firm—Eugene E. Renz, Jr.

[57] ABSTRACT

In a welding mask assembly, a shield section having a viewing port defined by a peripheral frame; a lens pack mounted in the port; a cover member; and cooperating locking elements between the cover member and the frame. The cover member operates between a locked position supporting the lens pack in the port and a released position permitting removal of the lens pack upon lateral movement of the cover member relative to the frame in only one predetermined plane. A spring element normally biases the cover member away from the plane.

9 Claims, 3 Drawing Sheets

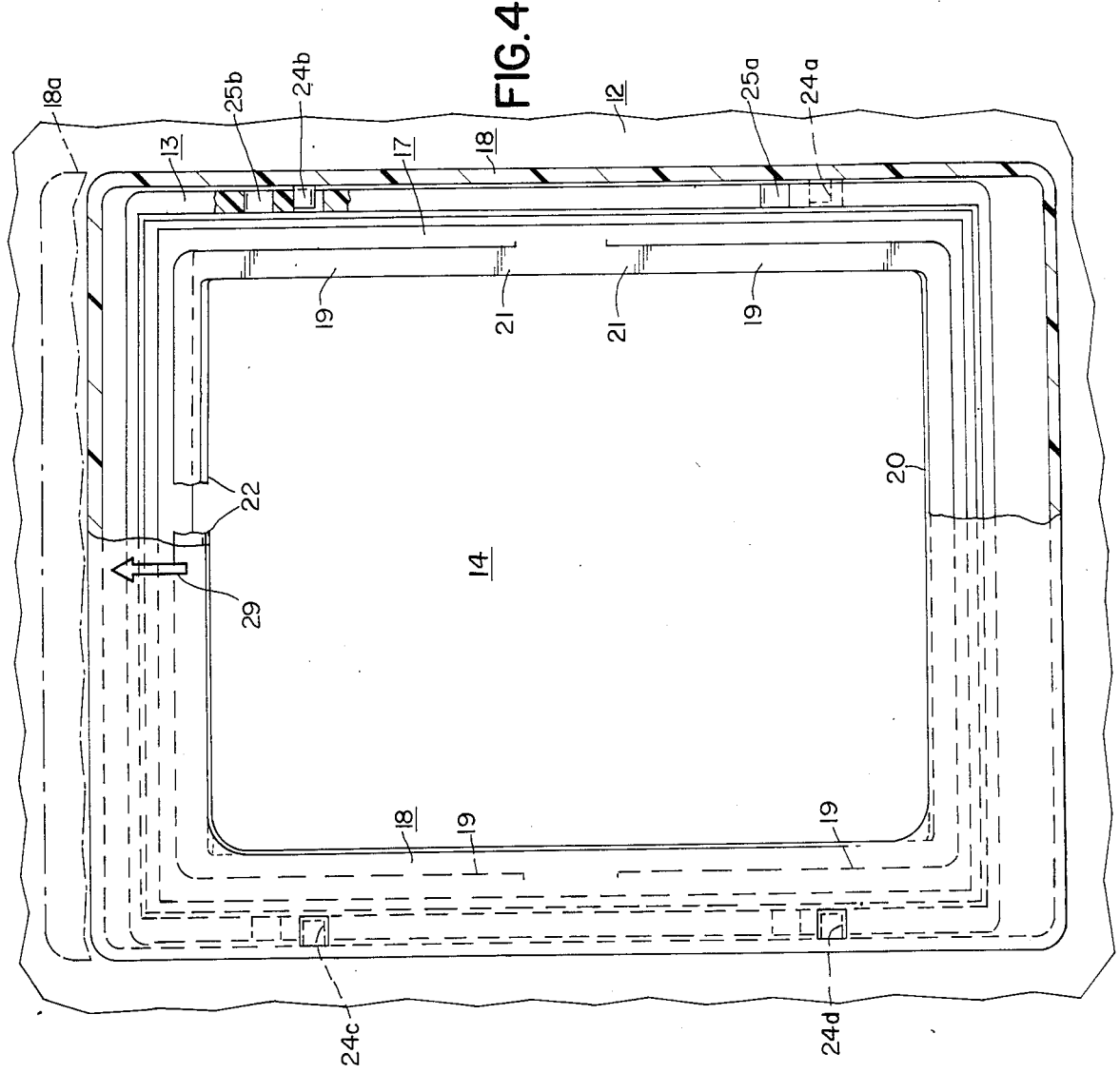
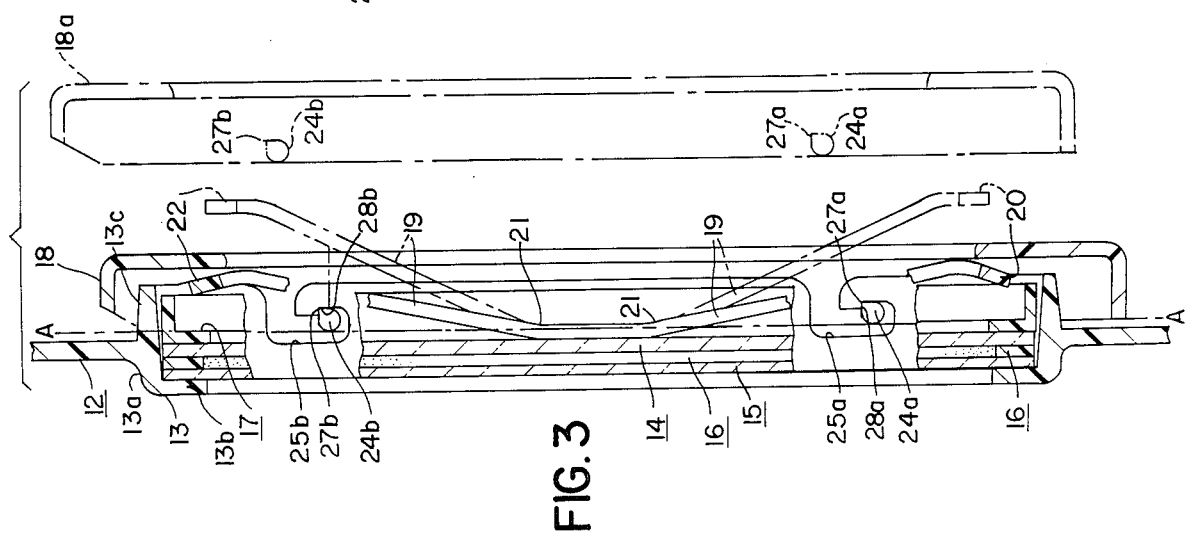

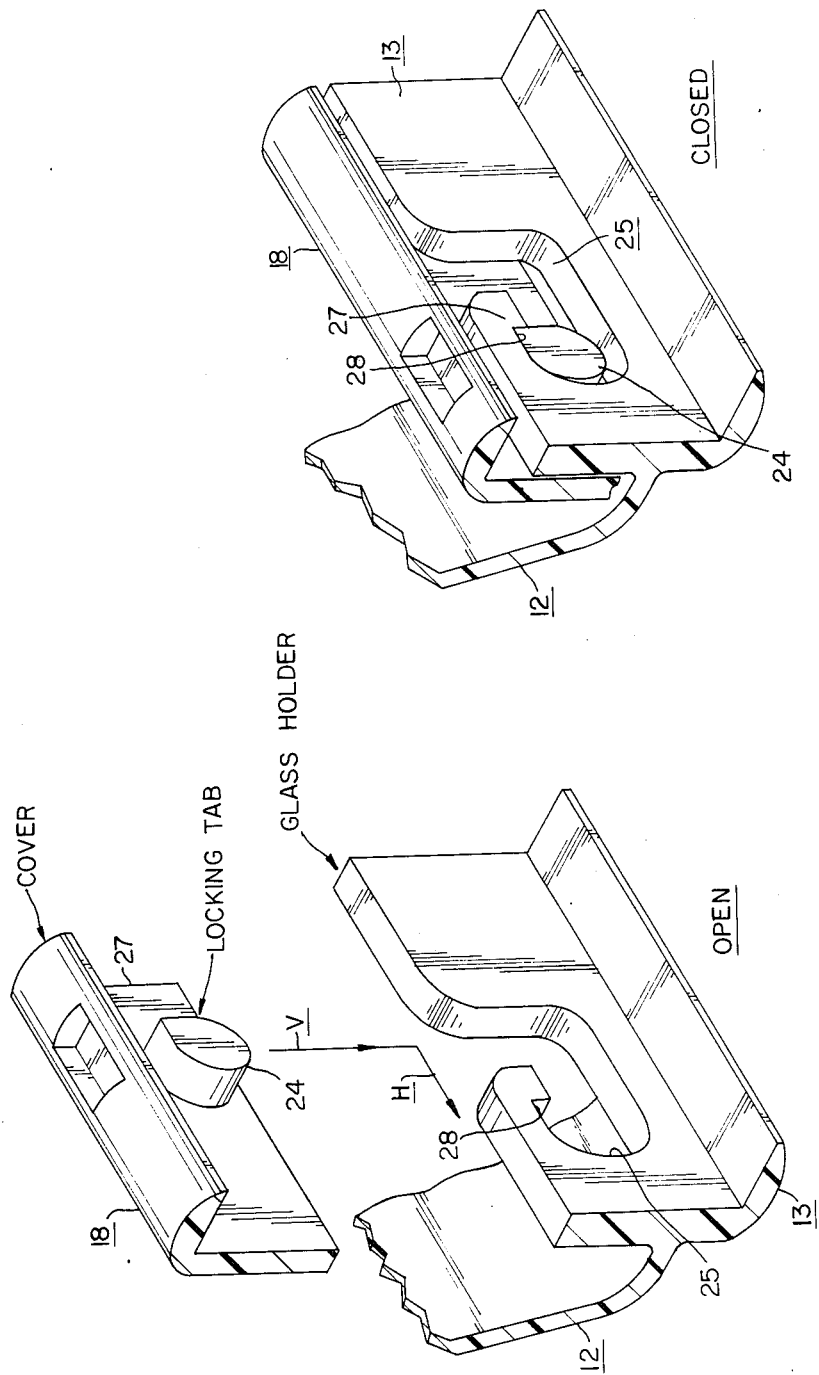

WELDING MASK LENS SPRING AND FLASH BARRIER

FIELD OF THE INVENTION

The present invention relates to welding masks or shields and, more specifically, to a novel mounting arrangement which permits safe and positive installation and removal of a lens pack containing the flash barrier lens system.

BACKGROUND OF THE INVENTION

The general construction and arrangement of welding masks or shields are not new. Typical prior art welding masks or shields are shown in various prior United States patents including the following: R. Malcolm, U.S. Pat. No. 1,904,993, issued Apr. 25, 1933; N. Anderson, U.S. Pat. No. 3,257,667, issued Jan. 28, 1966; J. N. Simpson et al, U.S. Pat. No. 3,458,865, issued Aug. 5, 1969; and Walters et al, U.S. Pat. No. 4,354,279, issued Oct. 19, 1982.

These prior art masks are generally of similar construction and comprise a shield section, preferably curved to conform somewhat to the face of the wearer. The shield section is preferably molded as a unit from an opaque, plastic, lightweight, stiff material. The shield is normally worn on the head of the user and includes some type of head band so it may be pivoted upwardly when not in use and easily moved to a face-protecting position.

When in a face-protecting position, the shield is faced forwardly of the wearer's face and extends around the side of the wearer's head so as to cover the head. The shield is usually provided with an enlarged, rectangular opening within which is mounted a lens assembly consisting of a plurality of panes, including, for example, an outer pane formed from a transparent material such as glass, an inner pane formed of similar material but which is tinted, colored or otherwise treated to eliminate the transmission of harmful radiation to the eyes of the wearer. Such radiation may be produced when contact is made between an energized welding rod and a work piece. The panes are usually separated by a gasket and are of a peripheral dimension conforming generally to the shape of the pocket-like viewing port in the shield but slightly undersized so that they may be easily assembled therein.

Typically, the panes of the lens assembly are oftentimes supported in the rectangular opening by means of a spring clip. The deficiencies of such an arrangement have been noted in U.S. Pat. No. 4,354,279. The mounting means described in that patent combines the insert and a spring clip into a unitary piece. An insert is provided which effectively blocks external light rays which might produce a corona or halo effect interiorly of the welding mask. A spring clip is provided which has horizontal leg portions pressing the insert against the lens pack.

The Walters et al design is admirably suited for providing an adequate corona barrier. Nevertheless, while the positioning of the lens pack is in a protected position to prevent penetration of harmful rays to the interior of the mask, the use of a spring clip is not totally satisfactory as a mounting means. The spring clip is somewhat clumsy and awkward to assemble and disassemble and can be inadvertently engaged to release the lens pack. What would be an improvement would be a system that is easy and quick to assemble and disassemble and will allow the lens pack to be removed only when a deliberate action by the operator is made but which cannot be accomplished unintentionally. Elimination of any wire which can come loose and harm the user is, of course, highly desirable.

SUMMARY OF THE INVENTION

The present invention relates to a welding mask assembly which comprises a shield section having a viewing port that is defined by a peripheral frame. The lens pack is mounted in the viewing port and a cover member covers the lens pack on the interior side of the shield. A cooperative locking means is provided between the cover member and the frame of the viewing port. The cover member is operable between a locked position which supports the lens pack in the port and a released position which permits removal of the lens pack. Movement between these two positions is achieved by lateral movement of the cover member relative to the frame in only one predetermined plane. Also, a biasing means is provided to normally bias the cover member away from that one predetermined plane where movement is permitted, so that normally the cover member is in a locked position supporting the lens pack in the port.

In one embodiment, the biasing means includes a pair of opposed biasing members such that both of them apply a bias to the cover member forcing it away from the plane. In this instance, either one of them is sufficient alone to bias the cover member away from the plane and, of course, when the cover is not in that plane, it cannot be moved to the released position. The locking means which cooperate with the cover member and the frame normally prevent lateral movement of the cover member relative to the frame. Since overcoming the bias on only one of the opposed bias members requires that the other bias means prevent movement of the cover in a lateral plane relative to the frame, the inclusion of a pivot means in the biasing means can transmit additional biasing force to the member which remains in the locked position.

BRIEF DESCRIPTION OF THE DRAWINGS

These and other objects of the present invention and the various features and details of the operation and construction thereof are hereinafter more fully set forth with reference to the accompanying drawings, wherein:

FIG. 3 is an enlarged, sectional, elevational view taken along the line 3—3 of FIG. 1 showing in detail the elements of the lens pack and cover member in cooperation with the frame as a stacked and locked operational mode of the device shown in FIG. 2. In addition the lens cover is shown in a removed position in phantom line and the spring elements of the biasing means are shown in phantom line illustrating the released position, when the lens cover may be removed.

FIG. 4 is an enlarged, rear elevational view of the combination of lens pack and biasing means along with the cooperating frame and cover assembly, as shown in FIG. 3, with certain parts broken away in section for greater clarity of detail.

FIGS. 5 and 6 are greatly enlarged, cut-away details of the specific cooperating locking means shown both in an open and closed position in FIGS. 5 and 6, respectively.

DETAILED DESCRIPTION OF THE PREFERRED EMBODIMENT

Figure 1:
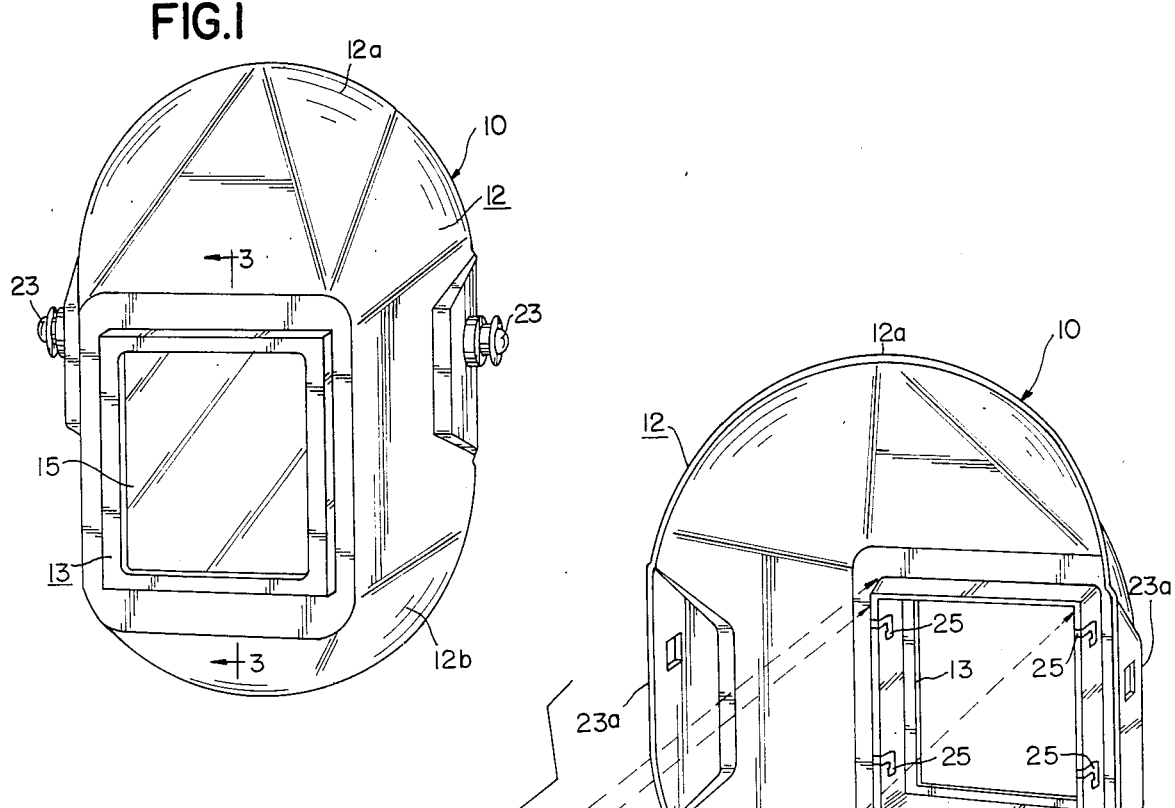
FIG. 1 is a perspective view of an ultra-light welder's helmet, incorporating the combination lens, spring and flash barrier assembly of this invention as viewed from the front.

Referring now to the drawings, and particularly to FIG. 1 thereof, there is shown a typical face-protecting device generally designated by the numeral 10. This device is particularly adapted for use by welders and is commonly referred to as a welding mask. The general configuration and arrangement of the welding mask are well-known and include a shield section 12, which is preferably curved to conform generally to the shape of the wearer, and includes the dome-like cover section 12a extending upwardly and rearwardly from the top of the shield section 12 and a lower section 12b extending downwardly and rearwardly from the lower edge of the shield section. These sections are gnerally integral and preferably molded as a unit from an opaque, plastic, lightweight, stiff material. The shield section 12 usually is connected to a head band, such as through head band supports 23, so that the mask can be pivoted between a face-protecting position covering the face and the ears of the user to a position above the head of the user when it is not in use.

The shield section 12 is usually provided with an enlarged viewing or opening port which is defined in FIG. 1 by peripheral wall 13 and which permits the user to observe his work. The peripheral wall 13, which is generally rectangular in shape in many cases, projects outwardly from the shield section 12 to accommodate a lens assembly as described herein and has an outwardly projecting generally rectangular peripheral wall section 13a and an inwardly directed wall section 13b projecting from the outer edge of wall 13b defining the viewing port. The wall 13a has an inward projection 13c formed integrally therewith (see FIG. 3) to define a pocket for the elements of the lens assembly.

Of primary importance in the lens assembly is a filter plate 14 which is adapted to eliminate the transmission of harmful light rays to the eyes of the wearer produced, for example, when contact is made between an energized welding rod and a work piece.

Figure 2:
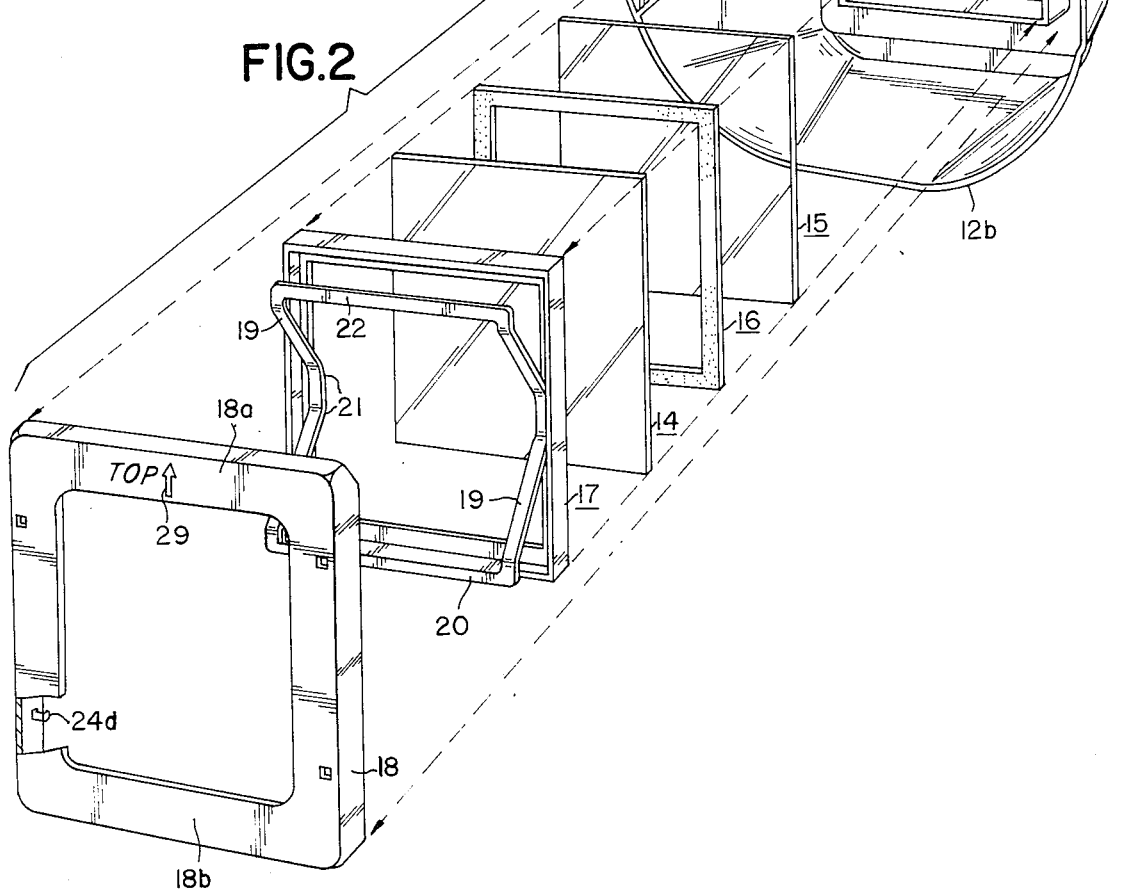
FIG. 2 is an exploded perspective view of the helmet and its associated lens, spring and flash barrier assembly as viewed from the rear, the adjustable head support bands and attachments being deleted for greater clarity of detail.

Shown in FIG. 2 is the lens pack which has been expanded. The shield section 12 is seen from the reverse side with head support openings 23a designated to show the location of the head band piece which is not shown in this view because it does not form a part of the present invention and would merely obstruct a line of sight to the features being described herein.

The lens assembly includes an outer pane 15 which is formed from a transparent material such as glass or impact resistant plastic and which is relatively inexpensive. This outer pane 15 is subjected to damage from sparking, smoke and other by-products of the welding operation and normally needs to be replaced fairly frequently. Since is is a relatively inexpensive piece, this outer pane 15 can easily be replaced when the lens pack is removed according to the present invention. Replacement of the outer pane 15 is easy for the welder to accomplish. In between the outer pane 15 and the filter plate 14 is a gasket 16 which is placed to prevent direct contact between the two glass-like materials. This is easily accomplished by the present invention. The pack, as shown in FIG. 2, includes the outer lens 15, the gasket 16, the filter plate 14 and a lens spring assembly 17. All of these internal components are contained in the frame 13 by the cover 18 as described hereinafter and can be removed, cleaned, and/or replaced without the use of tools.

In order to understand the operation of the locking mechanism of the preferred embodiment, reference is hereby made to FIG. 3 in which plane A—A is identified. This plane A—A is the only plane in which it is possible to have lateral movement of the cover 18 relative to the frame 13 towards a released position permitting removal of the lens pack from the port. The outer pane 15, gasket 16, filter 14 and lens spring assembly 17 are placed inside frame 13 and are held in place temporarily by gravity since the outer pane 15 and other components are larger than the port defined by frame 13. The cover shown in a removed position as 18a is then placed over the frame 13 and pressed directly down in a direction perpendicular to plane A—A. When this pressure is applied, both end 20 and end 22 of dual spring 19 are compressed and the dual spring 19 pivots about hinge 21.

As shown in FIG. 5, as the cover 18 is pushed in the direction of descending or vertical arrow V, the locking tab 24 is positioned inside slot 25 of frame 13. Movement of the cover 18 in the direction of arrow H along the horizontal will position the tab 24 to the closed end of slot 25. In the embodiment shown in FIGS. 5 and 6, the tab 24 has a point 27 which cooperatively locks into the edge 28 on slot 25. If pressure is then released so the biasing forces of dual spring 19 are allowed to function, the cover 18 is urged in the direction opposite arrow V so locking tab 24 is securely positioned in slot 25 by point 27 and edge 28. Because the slot 25 has been properly sized, the locking tab 24 is unable to move in any direction until the bias from dual spring 19 is overcome. While it remains in the position shown in FIGS. 3 and 6, the lens pack is maintained in a safe and secure position.

When it is desired to remove the lens pack for whatever reason, the operator can easily remove it. In order to accomplish this task, the bias of dual spring 19 must be overcome both at the first end 20 and at the second end 22. As long as locking tab 24 is securely held in slot 25 so the point 27 engages the edge 28, the case 18 cannot move in the direction shown by arrow 29 of FIG. 4. If pressure is applied to the cover 18 near 29, for example, the second end 22 of dual spring 19 would be compressed and the point 27b on the tab 24b would be separated from edge 28 of slot 25. Effectively, tab 24 would then be in plane A—A. Nevertheless, the cover 18 still cannot be moved and the lens pack cannot be removed because point 27a of the tab 24a is still engaged with edge 28a of slot 25a because the first end 20 of dual spring 19 has not been overcome.

If pressure is placed on the cover 18 at places adjacent both the first end 20 and the second end 22 of spring 19, then the entire cover is moved in the direction perpendicular to plane A—A and once the cover reaches the plane A—A, tab 24a is disengaged from slot 25a and tab 24b is disengaged from slot 25b so the cover member may now move between the locked position which supports the lens pack in the port to a released position which permits removal of the lens pack. This movement of the cover relative to the frame takes place only in plane A—A since it is only when the cover and frame are in this relative position that tabs 24a, 14b, 24c and 24d are disengaged from slots 25a, 25b, 25c and 25d. Movement of the cover permits removal of the cover to the position shown by 18a in FIG. 3. It is then a simple matter to lift out the lens spring assembly 17, the filter 14, gasket 16 and cover plate 15.

It is clear that the lens pack is secure when the cover 18 is cooperatively associated with the frame 13 in the locked position when tab 24 is engaged by slot 25. The dual spring 19 of the lens spring assembly 17 and the cushioning effect of gasket 16 prevent any relative movement. The welder can use the mask with the complete assurance that the lens pack will remain secure and undamaged. Even if the cover 18 is contacted through use, whether by intention or inadvertence, the lens pack will not move and will not become loose because of such contact. The cover member is only operable between its locked position which totally supports the lens pack and the release position which allows removal of the lens pack upon lateral movement of the cover when that cover is in that predetermined plane A—A. The user is totally protected from any springs or other protuberances which might be of concern if they were present. If desired, the front face of the latching cover 18 may be marked adjacent the arrow 29 with suitable indicia such as "TOP" to aid the user in positioning the latching cover to lock the parts in place. This orientation is necessary to ensure correct orientation and interaction between the bayonet slots 25 in inner wall 13c of the frame 13 and the latching pins or tabs 24a-24d of latching cover 18. As an additional visual aid in correctly orienting the latching cover, the top wall 18a may be made narrower than the opposite lower wall 18b, since the cover completely encloses all of the working mechanisms.

The novel mounting arrangement of the present invention also effectively shields or blocks out entrance of harmful light rays such as the ultra-violet radiation from a welding arc to the interior of the mask. More specifically, the mounting arrangement provides a dead end path to any light which may cause a halo effect in the peripheral area of the lens stack. More specifically, as best illustrated in FIG. 3, the frame 17a of spring assembly 17 is of angular profile and rectangular shape having right angularly disposed peripheral wall segments 17b, 17c which nest snugly in the walls 13 of the viewing port. Note the frame 17a corresponds closely dimensionally to the inside dimensions of the inner wall 13c defining the viewing port thereby blocking effectively the visible projection of radiation upon the peripheral walls of the viewing port.

While particular embodiments of the present invention have been illustrated and described herein, it is not intended to limit the invention and changes and modifications may be made therein within the scope of the following claims.

What is claimed is:

1. A welding mask assembly, comprising;
a shield section having a viewing port defined by a peripheral wall;
a lens pack mounted in said port;
a cover member;
cooperating locking means between said cover member and said peripheral wall;
said cover member operable between a locked position supporting said lens pack in said port and a released position permitting removal of the lens pack upon lateral movement of said cover member relative to said frame in only one predetermined plane; and
biasing means normally biasing said cover member away from said plane.

2. A welding mask assembly as claimed in claim 1, wherein said port is rectangular in shape and said biasing means includes means for biasing said cover member away from said plane at two non-adjacent sides of said rectangular port.

3. A welding mask assembly as claimed in claim 1, wherein said cooperating locking means includes a plurality of tabs mounted on said cover member and a plurality of cooperating slots formed in said peripheral wall, said tabs and said slots further including cooperative means for preventing lateral movement between said cover and said peripheral walls in said locked position.

4. A welding mask assembly as claimed in claim 3, wherein said tab includes a point adapted to engage the slot at an edge so as to prohibit relative movement of said cover with respect to said frame when said point engages said edge.

5. A welding mask assembly, comprising:
a shield having a generally rectangular viewing port defined by a peripheral wall;
a lens pack mounted in said port;
a cover member;
cooperating locking means between said cover member and said peripheral wall;
said cover member operable betwen a locked position supporting said lens pack in said port and a released position permitting removal of the lens pack upon lateral movement of said cover member relative to said frame and only one predetermined plane; and
biasing means comprising a dual biasing spring having a first end and a second end, said biasing spring permanently positioned to contact said cover member at two non-adjacent sides thereof.

6. A welding mask assembly, comprising:
a shield having a generally rectangular viewing port defined by a peripheral wall;
a lens pack mounted in said port;
a cover member;
cooperating locking means between said cover member and said peripheral wall;
said cover member operable between a locked position supporting said lens pack in said port and a released position permitting removal of the lens pack upon lateral movement of said cover member relative to said frame and only one predetermined plane; and
biasing means comprising a dual biasing spring having a first end and a second end, said biasing spring permanently positioned to contact said cover member at two non-adjacent sides thereof, said biasing means being centrally connected to a frame member of angular profile and rectangular shape corresponding to the dimensions of said viewing port and held in close proximity to said peripheral wall, thereby blocking effectively the visable projection of radiation upon said peripheral wall.

7. A welding mask assembly, comprising:
a shield having a viewing port defined by a peripheral wall;
a lens pack mounted in said port;
a cover member;
cooperating locking means between said cover member and said peripheral wall;

said cover member operable between a locked position supporting said lens pack in said port and a released position permitting removal of the lens pack upon lateral movement of said cover member relative to said frame and only one predetermined plane; and biasing means comprising a dual biasing spring having a first end and a second end, said biasing means permanently positioned to contact said cover member at two non-adjacent sides thereof.

8. A welding mask assembly, comprising:
a shield having a viewing port defined by a peripheral wall;
a lens pack mounted in said port;
a cover member;
cooperating locking means between said cover member and said peripheral wall;
said cover member operable between a locked position supporting said lens pack in said port and a released position permitting removal of the lens pack upon lateral movement of said cover member relative to said frame in only one predetermined plane; and
biasing means comprising a dual biasing spring having a first end and a second end, said biasing spring permanently positioned to contact said cover member at two non-adjacent sides thereof, said biasing means being centrally connected to a frame of angular profile and shape corresponding to the dimensions of said viewing port and held in close proximity to said peripheral wall, thereby blocking effectively the visable projection of radiation upon said peripheral wall.

9. A welding mask assembly, comprising;
a shield section having a viewing port defined by a peripheral wall;
a lens pack mounted in said port;
a cover member;
cooperating locking means between said cover member and said peripheral wall;
said cover member operable between a locked position supporting said lens pack in said port and a released position permitting removal of the lens pack upon lateral movement of said cover member relative to said frame in only one predetermined plane; and
biasing means normally biasing said cover member away from said one predetermined plane,
said cover member in said locked position immovable relative to said peripheral wall and releaseable from said peripheral wall only when disposed in a second plane parallel to said one predetermined first plane.

* * * * *